US012718931B2

(12) United States Patent
Hayes et al.

(10) Patent No.: US 12,718,931 B2
(45) Date of Patent: Aug. 25, 2026

(54) METHOD AND SYSTEM FOR GENERATING DENTAL IMAGES FROM MRI-DATA

(71) Applicant: Siemens Healthineers AG, Forchheim (DE)

(72) Inventors: Carmel Hayes, Munich (DE); Michaela Schmidt, Uttenreuth (DE); Andreas Greiser, Erlangen (DE); Jens Wetzl, Erlangen (DE); Marion Hellinger, Uttenreuth (DE)

(73) Assignee: Siemens Healthineers AG, Forchheim (DE)

( * ) Notice: Subject to any disclaimer, the term of this patent is extended or adjusted under 35 U.S.C. 154(b) by 149 days.

(21) Appl. No.: 18/740,936

(22) Filed: Jun. 12, 2024

(65) Prior Publication Data

US 2024/0412852 A1 Dec. 12, 2024

(30) Foreign Application Priority Data

Jun. 12, 2023 (EP) .................................... 23178700

(51) Int. Cl.
*G16H 30/40* (2018.01)
*G06T 7/00* (2017.01)

(52) U.S. Cl.
CPC ........... *G16H 30/40* (2018.01); *G06T 7/0012* (2013.01); *G06T 2207/10088* (2013.01); *G06T 2207/30036* (2013.01)

(58) Field of Classification Search
CPC ......... G06T 7/0012; G06T 2207/10088; G06T 2207/30036
See application file for complete search history.

(56) References Cited

U.S. PATENT DOCUMENTS

| | | | |
|---|---|---|---|
| 2009/0310846 | A1 | 12/2009 | Lemchen |
| 2018/0160932 | A1 | 6/2018 | Abkai et al. |
| 2022/0084267 | A1 | 3/2022 | Ezhov et al. |
| 2022/0335597 | A1 | 10/2022 | Shanbhag et al. |

OTHER PUBLICATIONS

"Three-dimensional localization of impacted teeth using magnetic resonance imaging" by O. Tymofiyeva et al. Clin Oral Invest. 14: 169-179. 2010.*

(Continued)

*Primary Examiner* — Jason M Ip
(74) *Attorney, Agent, or Firm* — Banner & Witcoff, Ltd.

(57) ABSTRACT

A method, system, and controller for generating dental images from magnetic resonance imaging (MRI) data are described. The method may include acquiring scout magnetic resonance (MR) images of a head, including a number of teeth of an upper and/or a lower jaw; automatically identifying the teeth in the scout MR images and determining positions of the identified teeth; defining a number of regions around the determined positions of the teeth, the regions representing a volume along a dental arch; acquiring a number of diagnostic MR images of at least the defined number of regions having a higher resolution than the scout MR images; generating a panoramic image based on the number of diagnostic MR images and the defined number of regions; and outputting the panoramic image.

20 Claims, 3 Drawing Sheets

(56) References Cited

OTHER PUBLICATIONS

"MRI of the teeth" by L.M. Tutton. Brit Journal Rad. 75, 2002, 552-562.*
"Automated Dental Arch Detection Using Computed Tomography Images" by T. Chanwimaluang et al. IEEE. 737-740.*
"Accuracy and efficiency of automatic tooth segmentation in digital dental models using deep learning" by J. Im et al. Scientific Reports. 9429, Jun. 8, 2002.*

* cited by examiner

S
T
R
R
R
A
D
A
R
R
P

L
T
L
L
L
T
L

METHOD AND SYSTEM FOR GENERATING DENTAL IMAGES FROM MRI-DATA

CROSS REFERENCE TO RELATED APPLICATIONS

This patent application claims priority to European Patent Application No. 23178700.3, filed Jun. 12, 2023, which is incorporated herein by reference in its entirety.

BACKGROUND

Field

The disclosure pertains to a method and a system for generating dental images from magnetic resonance imaging (MRI-data) as well as a controller for controlling am MRI system and a magnetic resonance imaging system.

Related Art

Dentists are used in their daily routine to look at panoramic radiography views based on 2D X-ray images that capture the entire mouth in a single projection, including the teeth, upper and lower jaws, surrounding structures and tissues. In the field of dental medicine, panoramic images (or "dental panoramic images") are images showing the teeth of a person in one 2D-image. Panoramic dental X-ray images (panoramic images acquired with X-ray) usually captures the oral cavity in one image, including the teeth, upper and lower jaws, surrounding structures and tissues. It is commonly performed by dentists and oral surgeons in everyday practice. Although, the dental arch is a curved structure, the panoramic image is a flat image of the curved structure. To achieve this, often a curved film is applied in the mouth for taking the panoramic image.

When scanning with magnetic resonance imaging, both, 2D and 3D imaging techniques can theoretically be used for dental views. However, up to now dentist hardly use MRI for imaging.

In typical MRI applications, plane slices can be chosen in 3D magnetic resonance (MR) images or stacks of 2D MR images and these slices can be reconstructed. However, since the dental arch is round, no panoramic images can be reconstructed with this technique. Thus, 3D images or 2D images in flat planes could be reconstructed very easily in MRI, but 2D images from curved planes are not available. it would be an advantage to use MRI even for dental imaging, since every X-ray imaging process goes along with radiation exposure for the patient.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
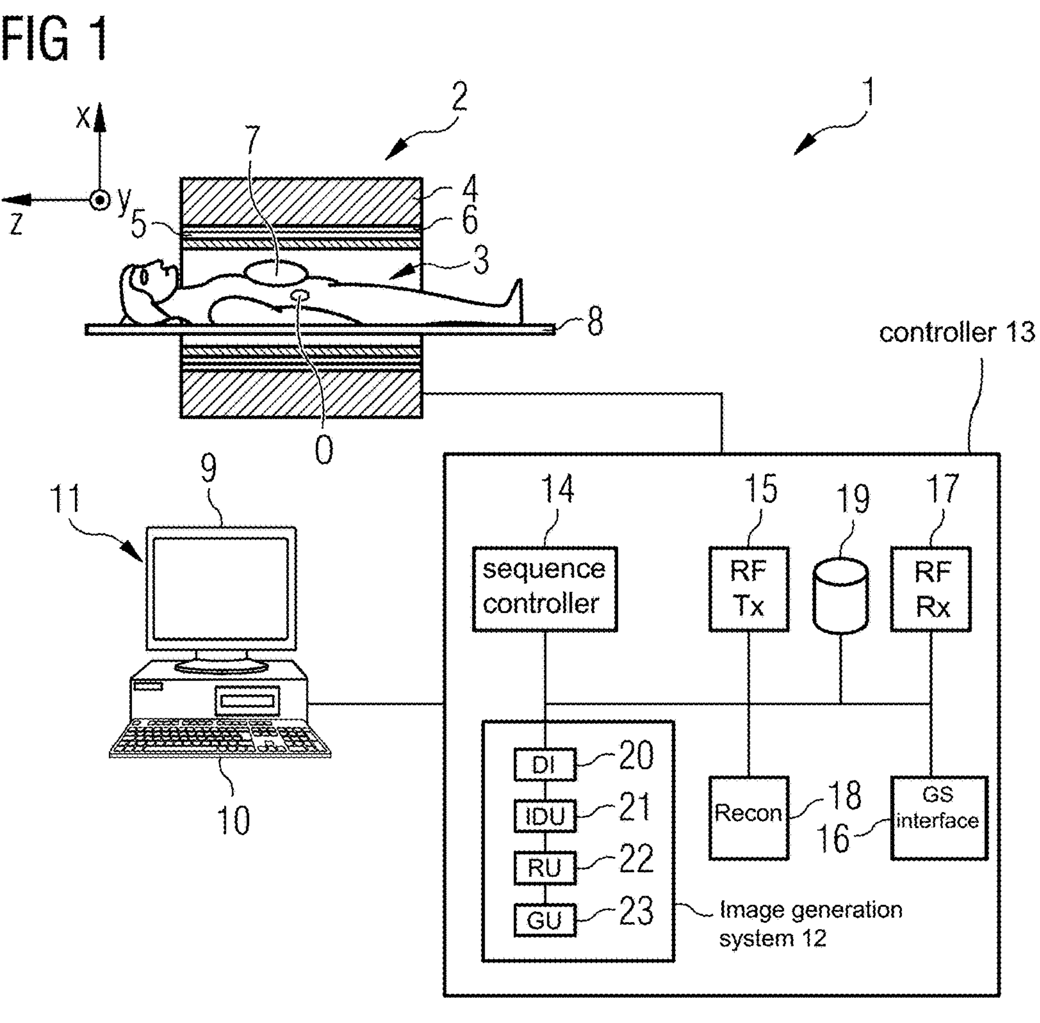
FIG. 1 shows a simplified MRI system according to exemplary embodiments of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure to improve the conventional systems and methods to facilitate the use of MRI for dental imaging, especially for panoramic imaging of the teeth.

This object is achieved by a method, a system, a controller, and a magnetic resonance imaging system (MRI-system) according to the present disclosure.

Typically, research work in dental MRI is performed using standard, manual (flat) slice positioning techniques, with no automation. For dental imaging, a 3D post-processing software is needed to create curved reformats for a panoramic view display. In the case of 2D imaging, or small field of view (FoV) 3D imaging, images of sub-regions of the tooth and jaw could be acquired (in difference to full volumetric coverage). These specific images could also be used for a panoramic image. However, the identification of these sub-regions and the prescription of slices to cover these regions is not easy. It typically requires a priori acquisition of a volume image to decide where the 2D slices or small 3D FoV should be positioned.

A method according to the disclosure for generating dental images from MRI-data, may comprise the following steps:

- acquiring scout MR-images of a head, comprising a number of teeth of an upper and/or a lower jaw,
- automatically identifying the teeth in the scout MR-images, and determining their positions,
- defining a number of regions around the determined positions of the teeth, the regions representing a volume along a dental arch,
- acquiring a number of diagnostic MR-images of at least the defined number of regions, having a higher resolution than the scout MR-images,
- generating a panoramic image based on the number of diagnostic MR-images and the defined number of regions, outputting the panoramic image.

In summary, it is derived from the scout images, which part of the image information is used from a high resolution acquisition in order to form a panoramic image.

The scout MR-images must at least comprise (i.e. show) a number of teeth of the upper and/or the lower jaw. The scout MR-images could comprise all teeth in the mouth of a person or a subset of teeth, only. They could show the jaws, only or the complete oral cavity. It could be advantageous, if they show the complete head. However, they could also show a part of the head, also, as long as the teeth are visible in the image. Especially, the number of scout MR-images cover the upper and lower jaw, including sinuses, and the temporomandibular joint. The scout images should be acquired with adequate spatial resolution and coverage such that algorithms capable of detecting teeth at root and crown level can be deployed. The scout MR-images are typically of a lower resolution than diagnostic MR-images.

The automatic identification of teeth in the scout MR-images could be performed by an algorithm configured for finding teeth in the image and determining their positions. Preferred algorithms are deep learning algorithms trained to identify teeth in the lower and upper jaws in MR-images, especially the molars, canine and front teeth of the upper and/or lower jaw.

Landmarks or image segmentation may be used to determine the position of a tooth. These landmarks are markers on the identified teeth, preferably at both root, and crown level, and allow the determination of the position of a tooth. The positions of the teeth allow the detection of the dental arch. For some applications the tooth root is more of interest, while for others the crown-to-root axis is of interest. It should be noted that the crown arch and the root arch are not necessarily parallel, thus, it is preferred that as well crown as also root of the teeth are identified. The landmarks can be used two-fold:

At first hand, they could be used to position 2D slices or small 3D volumes (field of view volumes) to image sub-regions of the teeth or jaw. For example, a combination of landmarks locating the canines and the molars of the lower jaw can be used to prescribe a slice or a stack of slices or a 3D volume aligned along the para-sagittal tooth axis. A preferred process comprises a determination of individual tooth planes, with the help of landmarks where the plane is in the sagittal tooth orientation, intersecting crown and root.

Secondly, the landmarks could be used to perform inline curved plane reformats (i.e. reformation of images to a flat plane from a curved plane) on high resolution 3D images (e.g. SPACE) visualizing a panoramic view similar to what the dentists are used. One major Difference is that with MR there is more than one view with higher resolution and contrast compared to X-ray.

Precise detection of dental landmarks is advantageous to plan 2D slices along the arch. These landmarks are therefore preferably a series of discrete points along an imaginary curve. The calculation of the geometric position and orientation of image-slices is preferably performed by interpolation between landmarks. This could be simple linear interpolation, but it could also involve mathematical functions e.g. cubic splines, higher-order polynomial functions etc.

The tooth planes are advantageous for planning the acquisition of slices of the diagnostic image or for image-reconstruction from k-space. Here it should be noted that (flat) planes may be constructed not only for single teeth, but also for groups of teeth. For example, regarding the molars, they nearly lie in one straight row. This row in addition with the line from crown to root of these teeth may be used to construct a flat plane passing through all molars. The same may be achieved by using the front teeth. Now, images could be recorded, wherein the image slices are arranged parallel to these planes and/or image slices could be reconstructed parallel to these planes. With this technique, the teeth could be recorded very effectively. Although the planes may be theoretically oriented in an arbitrary manner, as long as there is a defined reference to this orientation. However, it is preferred that the planes are parallel to the longitudinal axis and especially parallel to the sagittal plane.

However, for some applications or cases, it may be advantageous (as alternative or in addition to landmarks) to recognize the teeth in whole, especially in order to create a usable panoramic view with MR images. This is because of partial volume effects in the MR-images. This can preferably be achieved with an image segmentation process where each tooth and its roots is identified by a machine learning model trained for segmenting teeth in MR-images. Regarding a segmentation process, it could be sufficient to identify the best plane for each tooth.

When the positions of the teeth are known, there could be defined a region or a plurality of regions where the information of diagnostic MR-images should at least be fetched. This could at first hand reduce the data needed for the method, and secondly (and very important) gets rid of image information blurring the panoramic view on the teeth.

These regions should cover at least the whole volume of all identified teeth and as well some tissue around the teeth, e.g. the upper and lower jaw and preferably also sinuses and/or the temporomandibular joint. There could be chosen one large region covering all teeth of the complete dental arch (e.g. a coherent volume), a plurality of sub-regions (a plurality of separate or adjacent volumes), e.g. wherein four regions covering the four groups of molars (upper, lower, left and right) and two regions covering the other teeth (upper and lower), and/or a plurality of regions, wherein a region is defined around every identified tooth. A preferred region could also be one of the dental sextants or segments. The region(s) could also comprise only a part of the teeth.

Although the regions are just representations of (theoretical) volumes around the determined positions of the teeth, the form of the dental arch could be derived from the volumes. Altogether, the regions sum up in a total volume following the dental arch. Thus, the regions represent a volume along the dental arch.

It should be noted that when the positions of the teeth are known, the dental arch is also known, since it is the arch of the teeth. For defining the number of regions, it is also possible to define a dental arch as basis for the regions. This could be performed with a trained machine learning model, however, it is also possible to easily reconstruct a curved plane through the positions of the identified teeth (e.g. by a parable or with the help of a polynomial function). Nevertheless, since the positions of the teeth define the dental arch, a number of regions around the dental arch is also surrounding the determined positions of the teeth. However, it could be advantageous to first define a dental arch from the positions of the teeth in the case one single region (or an upper and a lower region) should be defined. Also, volumes around the teeth could be combined (e.g. with a logical OR combination) to form one single region.

Now, when a single region or a plurality of regions is defined, this region indicates, which image information of a diagnostic MR-image should be used for the panoramic image. In addition to the panoramic image, further images or views could be generated. A diagnostic MR-image has a higher resolution than the scout MR-image(s). Where the advantage of low-resolution scout MR-image(s) is that they could be acquired in a short time. The advantage of the high-resolution diagnostic MR-images is that they provide diagnostic information. A "diagnostic" MR-image could also be referred to as "clinical"- or "high resolution" MR-image. The fact that only a special number of regions is used for the panoramic image could lower the acquisition time for the diagnostic image, since only the information in the region(s) could be acquired.

It is possible to acquire one single diagnostic MR-image showing the complete oral cavity (or at least the teeth in the yaws). However, it is also possible that a diagnostic MR-image only shows a defined region and there could be a plurality of diagnostic MR-images showing every defined region. Thus, for the panoramic image, the regions could be "cut out" of the diagnostic image(s), but also only the region(s) could be recorded as diagnostic image(s).

When generating the panoramic image from the number of diagnostic MR-images, the defined number of regions must be considered. This could e.g. be done by cutting out these region(s) from a single 3D diagnostic MR-image. In the case, every diagnostic MR-image shows a 3D volume comprising a specific tooth, the determined positions of the teeth could be used to arrange these 3D volumes correctly to form a 3D arrangement of the dental arch.

An output image could in addition alter the view of the diagnostic MR-image. For example, the above cut-out or volume arrangement could be projected on a flat 2D plane in order to form a panoramic view. The output image could also be created with the help of the auto align algorithm applied to the scout images (to find the positions of the teeth). It does not necessarily have to display the entire dental arch, but could also show only a part of the teeth or just a segment of the arch.

The resulting panoramic image could then be outputted, e.g. on a display of an MRI system or a screen on the desk of a dentist. It is additionally possible to display a "preview" panorama generated from the scout image(s) and the number of regions.

The intention of the disclosure is to use the positions of the teeth (and regions around these teeth) in the scout image(s) to automatically plan slices or slabs for diagnostic clinical imaging.

Ideally, in a streamlined dental MRI workflow, the dentist or dental assistant operating a dental MR scanner, should not be concerned with the prescription of slices or volumes, as is currently the case in standard MR clinical practice of other organs and body parts. By using the method according to the disclosure, the user of a dental MR scanner receives a fully automatic slice and volume positioning software so that the device can be used in a so-called push-button fashion. The dentist is then able to obtain entire volumes and/or sub-volumes of the teeth and jaws, and these images could be displayed in a manner that is familiar to the dentist, e.g. in the form of a panoramic view. In one embodiment, the panoramic view may be displayed in the inline display right after the high resolution 3D scan is finished.

It is even conceivable that MRI can offer a superior 3D image visualization of all the teeth compared with standard radiographs, provided of course that each tooth can be segmented, in addition to the alveolar bone.

The stack of reformatted (thin) slices along the depth (distal or proximal) direction may be displayed as a movie loop, to account for remaining misalignment of the reformatted slices versus individual tooth orientation, allowing the reader to get a full "single display" view to all details or individual roots of each tooth without the need for segmentation, distorting of surrounding tissue or accepting partial volume effects due to thick slice MIP/MPR display.

In an exemplary embodiment, an annotation of the quadrants or even individual teeth are added to the panoramic image, especially in a dynamic fashion, e. g. by labelling individual roots in different frames of the movie loop. A selection of the scanning region (e.g. a quadrant) for subsequent targeted scan planning may be supported by clicking on an area in the displayed panoramic view.

A system according to the disclosure for generating dental images from MRI-data, especially by performing the method according to the disclosure, comprises the following components:

- a data interface configured for receiving scout MR-images of a head comprising a number of teeth of an upper and/or a lower jaw,
- an identification unit configured for automatically identifying the teeth and determining their positions in the scout MR-images,
- a region unit configured to define a number of regions around the determined positions of the teeth, the regions representing a volume along a dental arch,
- a data interface configured for outputting commands and/or information for acquiring a number of diagnostic MR-images of at least the defined number of regions, having a higher resolution than the scout MR-images, and for receiving this number of diagnostic MR-images,
- a generation unit configured for generating a panoramic image based on the number of diagnostic MR-images and the defined number of regions,
- a data interface (possibly the same as used for the scout MR-images) configured for outputting the panoramic image.

The functions of the units have already been explained above in the light of the method. The system may comprise a software unit for calculating and displaying the panoramic image.

A controller according to the disclosure for controlling a magnetic resonance imaging system comprises a system according to the disclosure and/or is configured to perform a method according to the disclosure.

A magnetic resonance imaging system according to the disclosure comprises a controller according to the disclosure.

Some units or modules of the system mentioned above can be completely or partially realized as software modules running on a processor of a respective computing system, e.g. of a controller (controller) of a magnetic resonance imaging system or of a diagnostic system. A realization largely in the form of software modules can have the advantage that applications already installed on an existing computing system can be updated, with relatively little effort, to install and run these units of the present application. The object of the disclosure is also achieved by a computer program product with a computer program that is directly loadable into the memory of a computing system, and which comprises program units to perform the steps of the inventive method, at least those steps that could be executed by a computer when the program is executed by the computing system. It should be noted that an application of a pulse sequence here means "sending control commands in order to control am MRI scanner to apply the pulse sequence". In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a computing system. A processor unit can comprise one or more microprocessors or their equivalents.

Particularly advantageous embodiments and features of the disclosure are given by the dependent claims, as revealed in the following description. Features of different claim categories may be combined as appropriate to give further embodiments not described herein.

According to a method, molars, canine and front teeth of the upper and/or lower jaw and possibly also positions of missing teeth are identified in the course of identifying the teeth.

In the case there are tooth gaps, the positions of the missing teeth could also be advantageous for the method. Thus, preferably also tooth gaps corresponding to missing teeth are identified in the scout MR-images. This could especially be achieved by determining a curved dental arch from the positions of the identified teeth and interpolating positions of missing teeth between detected teeth on the dental arch. Especially in the case of many missing teeth, but also in other cases, a curved dental arch could also be determined with the help of contrast differences between different bone types. Positions of missing teeth on the dental arch could then be interpolated based on the identified teeth (since it is clear how many and which teeth have been between these existing teeth) and/or based on the contrast differences (maybe the positions where the missing teeth have been visible in the bone of the jaws or the surrounding tissue).

A method determines the positions of missing teeth by interpolating between detected teeth along the curved dental arch. In fact, the shape of the dental arch can likely be described mathematically using e.g. a parabolic curve or a fourth-order polynomial. Machine learning software can be trained to recognize missing teeth when these are explicitly marked as missing in the annotation phase.

In a method according to an exemplary embodiment of the disclosure, landmarks are determined for a plurality of teeth, especially each tooth in the course of determining the positions of the identified teeth. This may include, for a tooth, identifying at least a point on a predefined position at the crown and a number of points at the end (the tip) of at least one root of this tooth. In an exemplary embodiment, the landmarks comprise information about the position of these points and/or lines through these points. For example, for any type of teeth, there may be defined special points for the landmarks, e.g. for the front teeth the tip of the crown and the end (tip) of the root and for molars the center of the crown and the ends (tips) of every root. Points on other positions of a tooth may also be added.

In a method according to an exemplary embodiment of the disclosure, a segmentation action is performed for a plurality of teeth, such as for each tooth (especially crown to root) in the course of determining the positions of the identified teeth. A machine learning model trained for image-segmentation may be used. The general architecture and training routines for such models are known in the art. A training may be achieved by inputting MR-images where the teeth are labelled. The result may be a rectangular volume around each tooth. In an exemplary embodiment, a volume element (e.g. such rectangular volume or any other volume surrounding the respective tooth) or at least a central line for every tooth (parallel to the lo longitudinal axis (perpendicular to the transverse plane showing the position of the respective tooth) is determined based on the results of the segmentation action.

In a method according to an exemplary embodiment of the disclosure, individual tooth planes of the teeth are determined with the help of the determined landmarks or based on the segmentation in the course of determining the positions of the identified teeth. The plane may be in the sagittal tooth orientation, intersecting crown and root(s) of a tooth, especially each tooth. However, it is not necessary that the plane is exclusively in the sagittal tooth orientation. Other planes may also (or additionally) be calculated and may be advantageous for special applications. Further planes may be the coronal plane or the axial plane. It should be noted that the sagittal, coronal, and axial planes are often referred to in dentistry as the longitudinal, cross-sectional and transverse planes.

In a method according to an exemplary embodiment of the disclosure, the landmarks and/or information from the segmentation is used to position 2D slices of the teeth or 3D field-of-view-volumes around the teeth to image sub-regions of the teeth or jaw. Such 3D field-of-view-volumes could directly be used as regions for the method. A suitable information from the segmentation is any information that defines the position of the respective tooth or teeth and especially also their orientation. Such information may be the position and the dimensions of a volume ("bounding box") around a tooth or easily a number of coordinates of a tooth, e.g. its center or points on the crown and on the roots.

In an exemplary embodiment of the disclosure a combination of landmarks and/or information from the segmentation locating teeth may be used to prescribe a slice or a stack of slices or a 3D volume aligned along the sagittal or longitudinal plane.

In a method according to an exemplary embodiment of the disclosure, the landmarks and/or information form the segmentation is used to perform inline curved plane reformats on the diagnostic MR-images. In an exemplary embodiment, the panoramic image provides (shows) a panoramic view of the dental arch. In an exemplary embodiment, the output is the display of the panoramic image in an inline display, e.g. right after the acquisition of the diagnostic MR-images is finished. The output of the image may be stored in a storage unit, especially a hard disk drive, an SSD storage or a random access memory (RAM) for further use.

Especially, the positions of the teeth or an interpolated dental arch is used to cut out image information from the diagnostic MR-image(s). For example, in the case, there is a 3D image, a U-form following the dental arch could be cut out. This image information may then be projected on a plane to result in a 2D panoramic image of the dental arch. Alternatively, the image following the dental arch could be "bent" to form a plane, what could also be used to form a panoramic view of the dental arch.

In a method according to an exemplary embodiment of the disclosure, the identification of teeth, and especially also the determination of their position, is performed with a deep machine learning algorithm trained on scout MR-images with labelled teeth. This algorithm may also be trained to recognize missing teeth by labelled tooth gaps in the scout MR-images.

In a method according to an exemplary embodiment of the disclosure, the identification of the teeth is performed in a plane at the roots of the teeth (at root level) and/or in a plane at the crowns of the teeth (at crown level of the teeth), especially at both levels.

In a method according to an exemplary embodiment of the disclosure, a movie loop is generated as output image in addition to the panoramic image. This movie loop may show slices of the number of diagnostic MR-images in form of a distal or proximal movement through the dental arch and is based on the number of diagnostic MR-images and the defined number of regions. This movie loop may be an image sequence showing a succession of slices of a stack of slices. It could also be an animated GIF. The movie loop is assigned or superimposed to regions in the diagnostic MR-images.

In a method according to an exemplary embodiment of the disclosure, a region is a bounding box (volume around a number of teeth) which marks a region of interest for the acquisition of the diagnostic MR-images. This region (bounding box) may be used for planning of slices for subsequent planar 2D scans. In an exemplary embodiment, the region is divided into quadrants and the output comprises an annotation of the quadrants and/or an addition of individual teeth. A region may especially be selected by a user. In an exemplary embodiment, a bounding box is defined which marks the region of interest in the following scans and which is then translated into an advantageous slice planning for the subsequent planar 2D scans.

In one embodiment, the image information used for detecting landmarks in the scout MR-images may be complemented by image information taken from the diagnostic MR-images, e.g. the tooth rows are defined based on the localizer data. Then, the algorithm uses this guidance to find the teeth in the high resolution dataset and defines a sub-volume in the high resolution dataset in which the automated individual tooth segmentation is performed. This may help to speed up the processing pipeline and it may also improve robustness, as the diagnostic MR-images may be acquired in a smaller volume.

It should be noted that according to the basic method, the teeth have to be identified in the scout MR-images and this information is used to create the panoramic image from the diagnostic MR-images. However, the additional feature that the scout MR-images may be complemented by image information taken from the diagnostic MR-images is no contradiction to this. There could advantageously be used an iterative process to extract the image information from the diagnostic MR-images by refining the information taken from the scout MR-images. Then, additional diagnostic MR-images may be acquired based on the refined information or sections cut out from diagnostic MR-images to form the panoramic image may be chosen based on the refined information.

In a method according to an exemplary embodiment of the disclosure, image information used for identifying the teeth in the scout MR-images is complemented by image information taken from the diagnostic MR-images for generating the panoramic image. Although the scout images have lower resolution than the diagnostic MR-images, they could nevertheless comprise advantageous information. Tooth rows may be defined based on the identified teeth in the scout MR-images, then this information is used as guidance to find the teeth in the diagnostic MR-images. A sub-volume in the diagnostic MR-images may then be defined in which an automated individual tooth segmentation is performed.

In a method according to an exemplary embodiment of the disclosure, a flat plane is defined based on the positions of a group of teeth, such as following the positions and the orientation of at least two teeth, wherein slices of the diagnostic images are recorded and/or reconstructed parallel to this plane.

The method allows an automatic view description for a user upon an automatic selection of the region of interest to scan. No manual post-processing is needed. Also, no knowledge how to perform curved plane reformats is necessary to get panoramic view displays. Suitable panoramic images are delivered by the system automatically inline.

FIG. 1 shows a schematic representation of a magnetic resonance imaging (MRI) system 1. The MRI system 1 includes the actual magnetic resonance scanner (data acquisition unit) 2 with an examination space 3 or patient tunnel in which a patient or test person is positioned on a driven bed 8, in whose body the actual examination object is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 is designed that MR-images can be recorded. It here is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central control device (controller) 13 that is used to control the MRI system 1. This central controller 13 (or "control unit" 13) includes a sequence controller 14 for measurement sequence control. With this sequence controller 14, the series of radio-frequency pulses (RF pulses) and gradient pulses can be controlled depending on a selected pulse sequence to acquire magnetic resonance images within a measurement session. For example, such a series of pulse sequence can be predetermined within a measurement or control protocol. Different control protocols for different measurements or measurement sessions are typically stored in a memory 19 and can be selected by and operator (and possibly modified as necessary) and then be used to implement the measurement. In an exemplary embodiment, the controller 13 includes processing circuitry that is adapted to perform one or more operations or functions of the controller 13. Additionally, or alternatively, one or more components of the controller 13 may include processing circuitry that is adapted to perform one or more respective operations or functions of the component(s).

To output the individual RF pulses of a pulse sequence, the central controller 13 has a radio-frequency (RF) transmission device (RF transmitter) 15 that generates and amplifies the RF pulses and feeds them into the RF transmission antenna system 5 via a suitable interface (not shown in detail). To control the gradient coils of the gradient system 6, the controller 13 has a gradient system interface 16. The sequence controller 14 communicates in a suitable manner with the radio-frequency transmission device 15 and the gradient system interface 16 to emit the pulse sequence.

Moreover, the controller 13 has a radio-frequency (RF) reception device (RF receiver) 17 (likewise communicating with the sequence controller 14 in a suitable manner) in order to acquire magnetic resonance signals (i.e. raw data) for the individual measurements, which magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed according to the present disclosure. The image data can then be outputted or stored in a memory 19.

Operation of the central controller 13 can take place via a terminal 11 with an input unit 10 (e.g., keyboard, mouse, touchscreen, etc.) and a display unit 9, via which the entire MRI system 1 can thus also be operated by an operator. MR images can also be displayed at the display unit 9, and measurements can be planned and started by means of the input unit (possibly in combination with the display unit 9), and in particular suitable control protocols can be selected (and possibly modified) with suitable series of pulse sequence as explained above.

The controller 13 may comprise a system 12 configured to perform the method according to the disclosure. This system 12 may comprises the following components that may appear to be software modules. The system may be referred to as image generation system or image generator.

A data interface 20 may be configured for the complete communication of the system with the other components of the MRI-system. It may have at least three functions:

1) receiving scout MR-images S of a head, comprising (showing) at least the teeth T in the upper and lower jaw,
2) outputting commands and/or information for acquiring a number of diagnostic MR-images D of at least a defined number of regions R, having a higher resolution than the scout MR-images S, and for receiving this number of diagnostic MR-images D, and
3) outputting the panoramic image P.

An identification unit 21 may be configured for automatically identifying the teeth T and determining their positions in the scout MR-images S.

A region unit 22 may be configured to define a number of regions R around the determined positions of the teeth T and provide them to the data interface 20 for the acquisition of diagnostic images D. The regions R represent a volume along and around the dental arch.

A generation unit (image generator) 23 may be configured for generating a panoramic image P based on the number of diagnostic MR-images D (received by the data interface 20) and the defined number of regions R. these panoramic images P are then sent to the data interface 20 in order to be outputted.

The MRI system 1 according to the disclosure, and in particular the controller 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
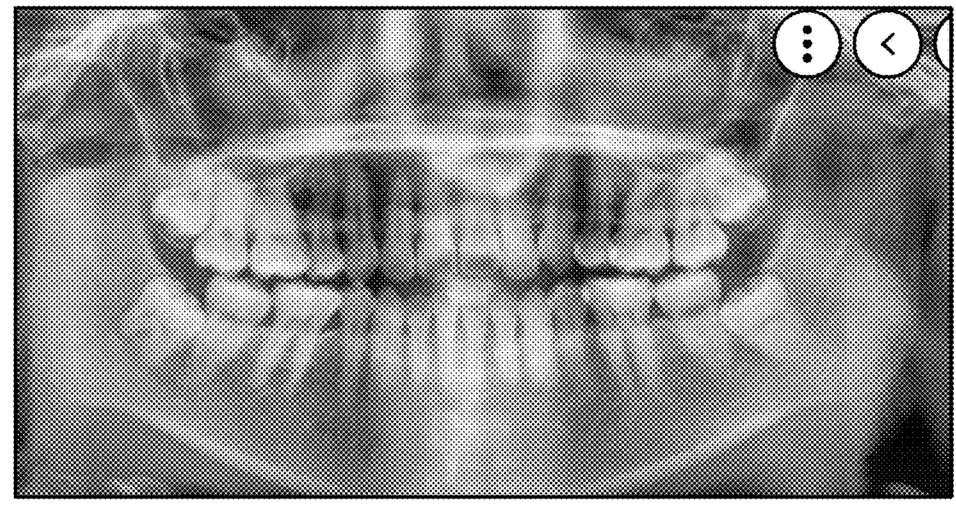
FIG. 2 shows a conventional, panoramic view of the teeth in the upper and lower jaw.

FIG. 2 shows a conventional panoramic view of the teeth in the upper and lower jaw. This is an X-ray image showing the teeth of a patient in one flat plane.

Figure 3:
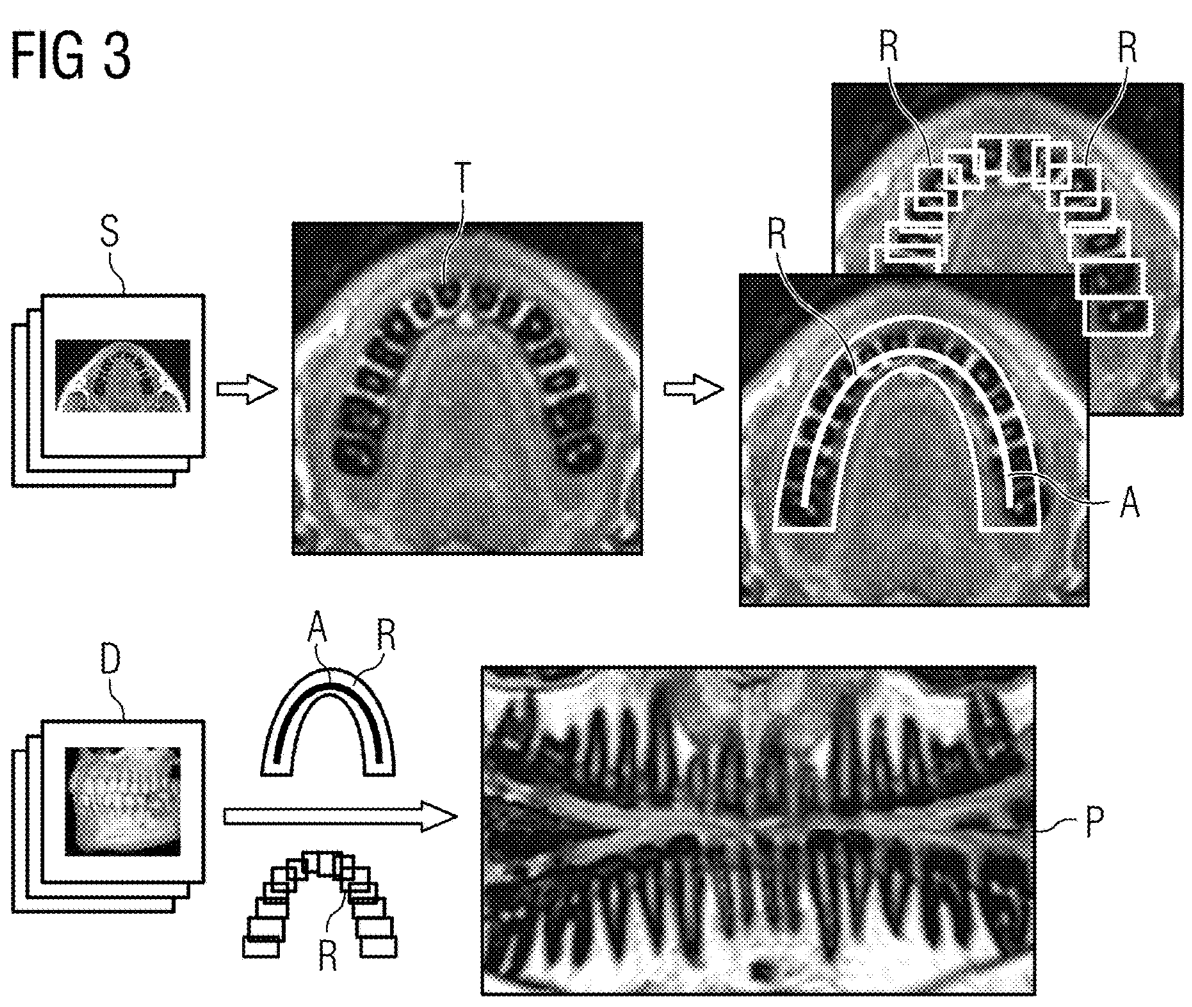
FIG. 3 is a flowchart of a method according to exemplary embodiments of the disclosure.

FIG. 3 outlines the method for generating dental images P from MRI-data. The upper row, shows the definition of regions R and the lower row the generation of a panoramic view as an example for a panoramic image P.

First, scout MR-images S of a head, showing at least the teeth T in the upper and lower jaw. Here, the scout MR-images S (left) are a stack low-resolution image slices. The shown view on the jaw should be an example for a full 3D-view of at least the oral cavity with the dental arch.

The upper picture in the middle outlines the automatic identification of teeth T in the scout MR-images S, and the determination of their positions. this could be done by defining landmarks L (see FIG. 4) or by image segmentation by a trained machine learning model.

Then, a number of regions R is defined around the determined positions of the teeth T. The upper picture on the right should show two possible results of forming regions R. There could be formed one single region R by deriving the dental arch A from the positions of the teeth (e.g. from landmarks L) and by constructing a region R around the deduced dental arch A. On the other hand, there could be formed many volumes (regions R) around the single teeth T (e.g. by segmenting the scout MR-images S by said model).

However, the regions R are defined, they cover a volume around the teeth that can be regarded as a field of view for diagnostic MR-images D acquired with a high resolution (see the left picture of the bottom row). These diagnostic MR-images D of at least the defined number of regions R.

As indicated over and under the bottom arrow, the regions R or the positions of the teeth T indicate the curve of the dental arch A as well as the image information that refer to the teeth T in the diagnostic MR-image D. This information could be cut out (or easily fetched in the case the diagnostic MR-image only shows the defined region(s) R and projected such that the resulting image is a panoramic view P (as an example for a panoramic image P).

The image information used for identifying the teeth T in the scout MR-images S could be complemented by image information taken from the diagnostic MR-images D for generating the panoramic image P. Tooth rows may be defined based on the identified teeth T in the scout MR-images S, then this information is used as guidance to find the teeth T in the diagnostic MR-images D. A sub-volume in the diagnostic MR-images D may then be defined in which an automated individual tooth segmentation is performed.

Figure 4:
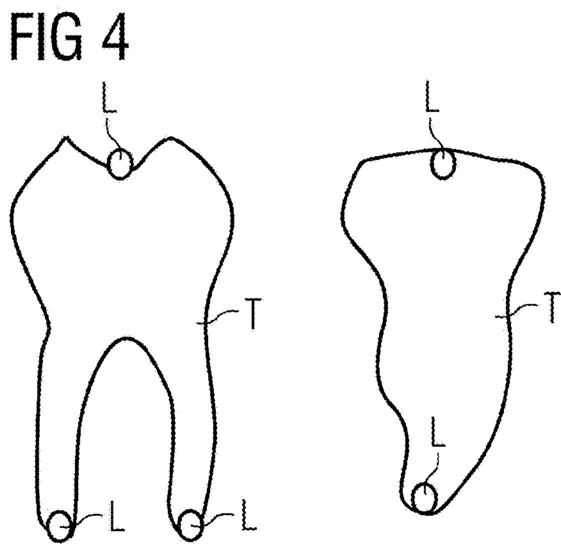
FIG. 4 shows landmarks on a tooth according to exemplary embodiments of the disclosure.

FIG. 4 shows an embodiment, where in the course of determining the positions of the identified teeth T, landmarks L are determined for each tooth T, wherein for each tooth T at least a point on a predefined position at the crown and a number of points at the end (tip) of at least one root of this tooth T are identified. The landmarks L comprise information about the position of these points. Individual tooth planes of the teeth T may be added with the help of the landmarks L, e.g. in the sagittal tooth orientation.

Figure 5:
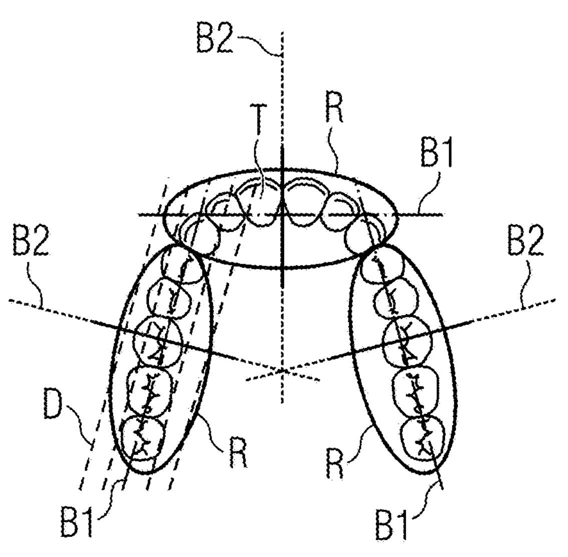
FIG. 5 shows a distribution of regions in the form of sextants according to exemplary embodiments of the disclosure.
Figure 5:
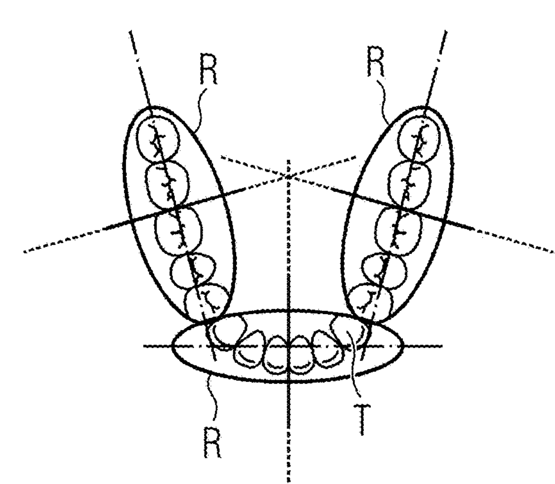

FIG. 5 shows a distribution of regions in the form of sextants. On the left, the teeth T of the upper yaw are shown and on the right the teeth T of the lower yaw. The teeth T are grouped in six groups (see circles) forming six sextants as regions R. For each sextant, planes are defined, a first plane B1 follows the row of teeth T, the second plane B2 follows the molars and pre-molars. Now, image acquisition could be planned, where the recorded image slices of the diagnostic image D are following these planes. In this example, the image slices are parallel to the first plane B1. They could also be recorded (or reconstructed from k-space) following the second plane B2. When all six sextants are recorded in "their direction", the panoramic image P could be generated.

Although the present disclosure has been disclosed in the form of exemplary embodiments, aspects, and variations thereon, it will be understood that numerous additional modifications and variations could be made thereto without departing from the scope of the disclosure. For the sake of clarity, it is to be understood that the use of "a" or "an" throughout this application does not exclude a plurality, and "comprising" does not exclude other steps or elements. The mention of a "unit" or a "module" does not preclude the use of more than one unit or module. The expression "pair" could mean not only two, but also a "set of". The expression "a number" means "at least one".

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

The various components described herein may be referred to as "modules," "units," or "devices." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such modules, units, or devices, as applicable and relevant, may alternatively be referred to herein as "circuitry," "controllers," "processors," or "processing circuitry," or alternatively as noted herein.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for generating dental images from magnetic resonance imaging (MRI) data, comprising:

acquiring scout magnetic resonance (MR) images of a head, including a number of teeth of an upper and/or a lower jaw;

automatically identifying the teeth in the scout MR images and determining positions of the identified teeth;

defining a number of regions around the determined positions of the teeth, the regions representing a volume along a dental arch;

acquiring a number of diagnostic MR images of at least the defined number of regions having a higher resolution than the scout MR images;

generating, based on the number of diagnostic MR images and the defined number of regions, a panoramic image and an image sequence, wherein the image sequence includes slices of the number of diagnostic MR images in a form of a distal or proximal movement through the dental arch; and outputting the panoramic image and the image sequence.

2. The method of claim 1, wherein, identifying the teeth comprises: identifying, in the scout MR images, molars, canine, front teeth, positions of missing teeth, and tooth gaps corresponding to the missing teeth of the upper and/or lower jaw, by:

determining a curved dental arch from the positions of the identified teeth and interpolating positions of missing teeth between identified teeth on the dental arch; or determining a curved dental arch based on contrast differences between different bone types, and interpolating positions of missing teeth on the dental arch based on: the identified teeth and/or the contrast differences.

3. The method of claim 1, wherein determining the positions of the identified teeth comprises:

determining landmarks for a plurality of teeth, wherein for a tooth, at least a point on a predefined position at a crown and a number of points at an end of at least one root of the tooth are identified, the landmarks including information about the position of the points and/or lines through the points; and/or performing a segmentation action for a plurality of teeth, using a machine learning model trained for image-segmentation, and determining a volume element or at least a central line for each tooth based on results of the segmentation action, wherein individual tooth planes of the teeth are determined based on the landmarks or based on the segmentation, where a plane is in a sagittal tooth orientation, intersecting a crown and a root of a tooth.

4. The method of claim 3, wherein:

the landmarks and/or the results from the segmentation is used to position 2D slices of the teeth or 3D field-of-view-volumes around the teeth to image sub-regions of the teeth or jaw; and a combination of landmarks and/or the results from the segmentation locating teeth is used to prescribe a slice, a stack of slices, or a 3D volume aligned along the sagittal or longitudinal plane.

5. The method of claim 3, further comprising perform inline curved plane reformats on the diagnostic MR images based on the landmarks and/or the results from the segmentation, wherein the panoramic image provides a panoramic view of the teeth in the upper and/or lower jaw, and outputting the panoramic image comprises displaying the panoramic image in an inline display.

6. The method according to claim 1, wherein the identification of teeth and the determination of their position is performed using a deep machine learning algorithm trained on scout MR images with labelled teeth, the algorithm also being trained to recognize missing teeth by labelled tooth gaps in the scout MR images.

7. The method according to claim 1, wherein the identification of teeth is performed in a plane at roots of the teeth and/or in a plane at crowns of the teeth.

8. The method according to claim 1, wherein:

a region is a bounding box marking a region of interest for the acquisition of the number of diagnostic MR images and which is used to plan slices for subsequent planar 2D scans; and a region is divided into quadrants and the output comprises an annotation of the quadrants and/or an addition of individual teeth, the region being selected by a user.

9. The method according to claim 1, wherein:

first image information used for identifying the teeth in the scout MR images is complemented by second image information taken from the diagnostic MR images for generating the panoramic image, tooth rows are defined based on the identified teeth in the scout MR images, and the second image information taken from the diagnostic MR images is used as guidance to find the teeth in the diagnostic MR images, a sub-volume in the diagnostic MR images being defined in which an automated individual tooth segmentation is performed.

10. A non-transitory computer-readable storage medium comprising instructions which, when executed by a processor, cause the processor to carry out the method of claim 1.

11. A magnetic resonance imaging system comprising a controller adapted to perform the method of claim 1.

12. A system for generating dental images from magnetic resonance imaging (MRI) data, comprising:

a data interface configured to receive scout MR images of a head, comprising a number of teeth of an upper and/or a lower jaw;

an identification unit configured to automatically identify the teeth and determine their positions in the scout MR images;

a region unit configured to define a number of regions around the determined positions of the teeth, the regions representing a volume along a dental arch;

a data interface configured to: output commands and/or information to acquire a number of diagnostic MR images of at least the defined number of regions having a higher resolution than the scout MR images, and receive the number of diagnostic MR images;

an image generator configured to generate, based on the number of diagnostic MR images and the defined number of regions, a panoramic image and an image sequence, wherein the image sequence includes slices of the number of diagnostic MR images in a form of a distal or proximal movement through the dental arch; and a data interface configured to output the panoramic image and the image sequence.

13. A controller adapted to control a magnetic resonance imaging device comprising the system according to claim 12.

14. An apparatus comprising:

one or more processors; and memory storing instructions that, when executed by the one or more processors, cause the apparatus to perform the method of claim 1.

15. The method according to claim 1, wherein the image sequence is a looped image sequence.

16. The method according to claim 1, wherein the image sequence is a movie loop.

17. A method for generating dental images from magnetic resonance imaging (MRI) data, comprising:

acquiring scout magnetic resonance (MR) images of a head, including a number of teeth of an upper and/or a lower jaw;

automatically identifying, based on first image information, the teeth in the scout MR images, and determining positions of the identified teeth;

defining tooth rows based on the identified teeth in the scout MR images;

defining a number of regions around the determined positions of the teeth, the regions representing a volume along a dental arch;

acquiring a number of diagnostic MR images of at least the defined number of regions having a higher resolution than the scout MR images;

complementing the first image information with second image information that is based on the number of diagnostic MR images;

identifying the teeth in the number of diagnostic MR images based on the second image information;

defining a sub-volume in the number of diagnostic MR images in which an automated individual tooth segmentation is performed;

generating a panoramic image based on the number of diagnostic MR images, the defined number of regions, and the automated individual tooth segmentation; and outputting the panoramic image.

18. A non-transitory computer-readable storage medium comprising instructions which, when executed by a processor, cause the processor to carry out the method of claim 17.

19. A magnetic resonance imaging system comprising a controller adapted to perform the method of claim 17.

20. An apparatus comprising:

one or more processors; and memory storing instructions that, when executed by the one or more processors, cause the apparatus to perform the method of claim 17.

* * * * *